United States Patent [19]

Hess

[11] Patent Number: 5,700,237

[45] Date of Patent: Dec. 23, 1997

[54] DEVICE FOR CORRECTING ANKLE CONTRACTURES

[75] Inventor: Clarence E. Hess, Safety Harbor, Fla.

[73] Assignee: Restorative Care of America Incorporated, Clearwater, Fla.

[21] Appl. No.: 558,199

[22] Filed: Nov. 16, 1995

Related U.S. Application Data

[63] Continuation of Ser. No. 209,242, Mar. 14, 1994, abandoned.

[51] Int. Cl.$^6$ ............................................ A61F 5/00
[52] U.S. Cl. ............................ 602/27; 602/16; 602/28
[58] Field of Search .......................... 602/5, 16, 23, 602/27–29; 128/887, 892

[56] References Cited

U.S. PATENT DOCUMENTS

| | | |
|---|---|---|
| Re. 27,957 | 4/1974 | Larson . |
| 114,669 | 5/1871 | Grant . |
| 282,491 | 8/1883 | Burns . |
| D. 317,651 | 6/1991 | Farris . |
| D. 326,948 | 6/1992 | Williams et al. . |
| D. 338,273 | 8/1993 | Williams . |
| 433,227 | 7/1890 | Beacock . |
| 735,860 | 8/1903 | Darby . |
| 839,223 | 12/1906 | Stevens . |
| 1,332,047 | 2/1920 | Lasher . |
| 1,334,596 | 3/1920 | Crouch . |
| 1,402,282 | 1/1922 | Chevrier . |
| 1,656,322 | 1/1928 | Fischer . |
| 1,769,681 | 7/1930 | Ettinger . |
| 1,948,534 | 2/1934 | Nelson et al. . |
| 2,492,920 | 12/1949 | Koster . |
| 2,567,195 | 9/1951 | Ellery . |
| 2,847,991 | 8/1958 | Andrews . |
| 3,086,522 | 4/1963 | Frohmader . |
| 3,171,407 | 3/1965 | Rogers . |
| 3,304,937 | 2/1967 | Callender, Jr. . |
| 3,345,654 | 10/1967 | Noble . |

(List continued on next page.)

OTHER PUBLICATIONS

DePuy Fracture Appliances Catalogue, p. 101; DePuy Combination Leg Splint.
Feick Brothers Co., Seventh Edition, Illustrated Catalogue (1921), pp. 382 & 383.
Ponseti Lower Extremity Braces, pp. 435–1941 Zimmer Fracture Equipment (1955).
Zimmer Mfg. Co. Warsaw, Indiana, pp. 13, 31, 38.
Jun. 11, 1967 Newspaper Article—*Providence Sunday Journal Business Weekly*.
Theraboot Brochure.
E–Z Book Brochure.

*Primary Examiner*—Linda C. Dvorak
*Attorney, Agent, or Firm*—Zarley, McKee, Thomte, Voorhees, & Sease

[57] ABSTRACT

A therapeutic device for correcting ankle contractures affecting the angle between the leg and foot including a generally L-shaped two-piece frame having a leg portion and a foot rest portion pivotally connected to the leg portion; and adjustable length ankle strap mounted on the frame for securing the frame to the ankle; a pair of adjustable length tension adjusting straps which are operatively mounted between the leg portion and the foot portion for putting steady yet releasable pressure for decreasing the angle between the leg portion and foot portion such that tension is applied to the ankle and the foot is drawn closer to the leg. Furthermore, a laterally split anklet having right and left flaps releasably fastenable to each other and pockets which slide over the free ends of the frame portions is detachably connected thereto. The anklet wraps around parts of the foot and leg to cushion and protect them from direct contact with the frame. The anklet holds the leg and foot to the frame. Attached to the anklet on opposite sides thereof adjacent the top is a pair of loops for receiving ends of the tension adjusting straps while the other end of the straps are attached to opposite sides of the anklet adjacent the forward end thereto. The straps limit the angular movement of the foot and leg portions. Loops and hooks fasteners are utilized on the flaps and straps to provide the releasable adjustability needed to accomplish their stated functions.

30 Claims, 2 Drawing Sheets

U.S. PATENT DOCUMENTS

| | | |
|---|---|---|
| 3,523,526 | 8/1970 | Phelps . |
| 3,527,209 | 9/1970 | Baker . |
| 3,557,782 | 1/1971 | Wafer . |
| 3,584,622 | 6/1971 | Domemco . |
| 3,589,359 | 6/1971 | Hill . |
| 3,606,884 | 9/1971 | Pettine . |
| 3,618,946 | 11/1971 | Lee . |
| 3,779,654 | 12/1973 | Horne . |
| 3,805,773 | 4/1974 | Sichau . |
| 3,976,059 | 8/1976 | Lonardo . |
| 4,955,370 | 9/1990 | Pettine . |
| 5,151,081 | 9/1992 | Williams . |
| 5,154,695 | 10/1992 | Farris et al. . |
| 5,197,942 | 3/1993 | Brady . |
| 5,224,925 | 7/1993 | Varn . |
| 5,269,748 | 12/1993 | Lonardo . |
| 5,298,013 | 3/1994 | Lonardo . |
| 5,367,789 | 11/1994 | Lamont . |

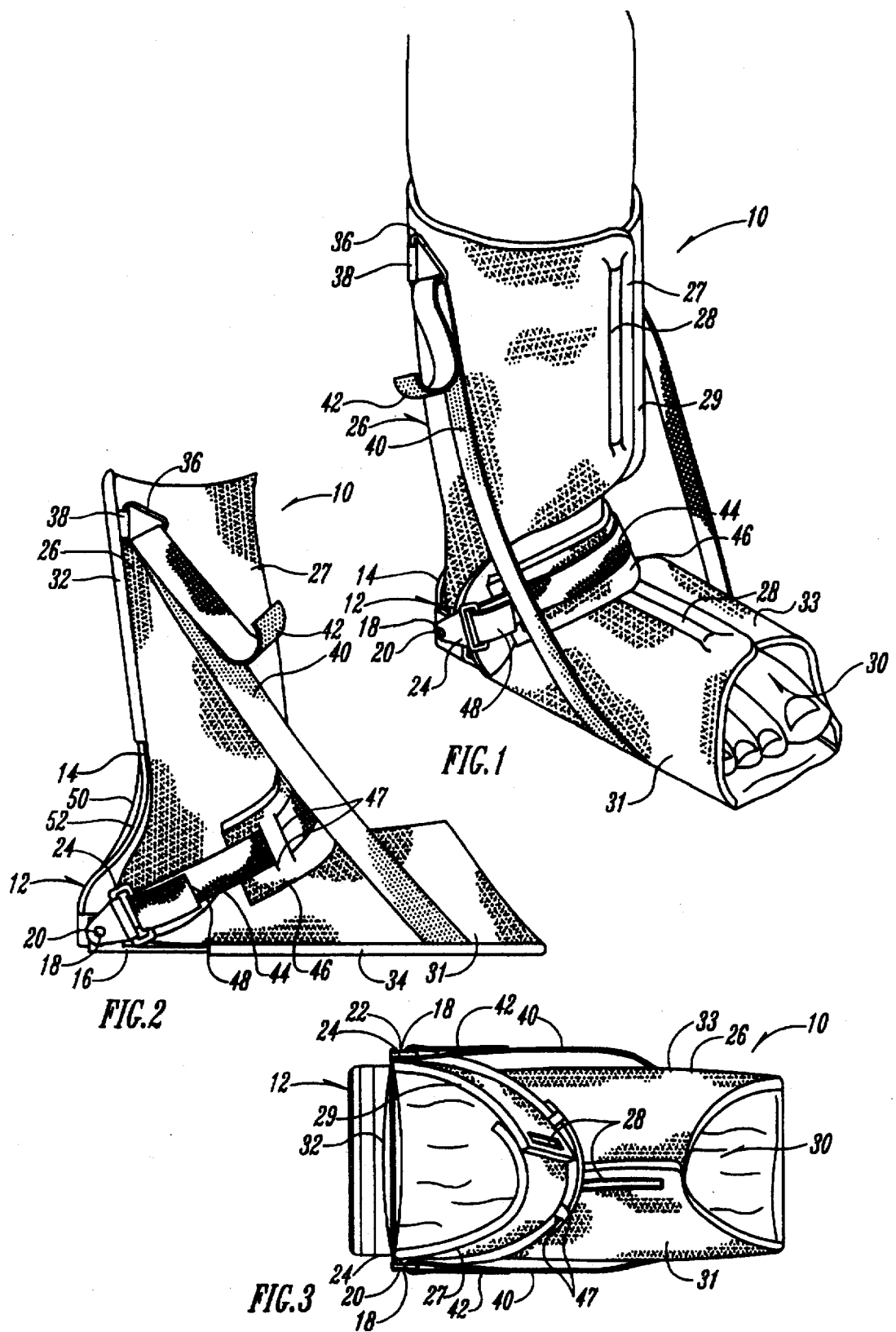

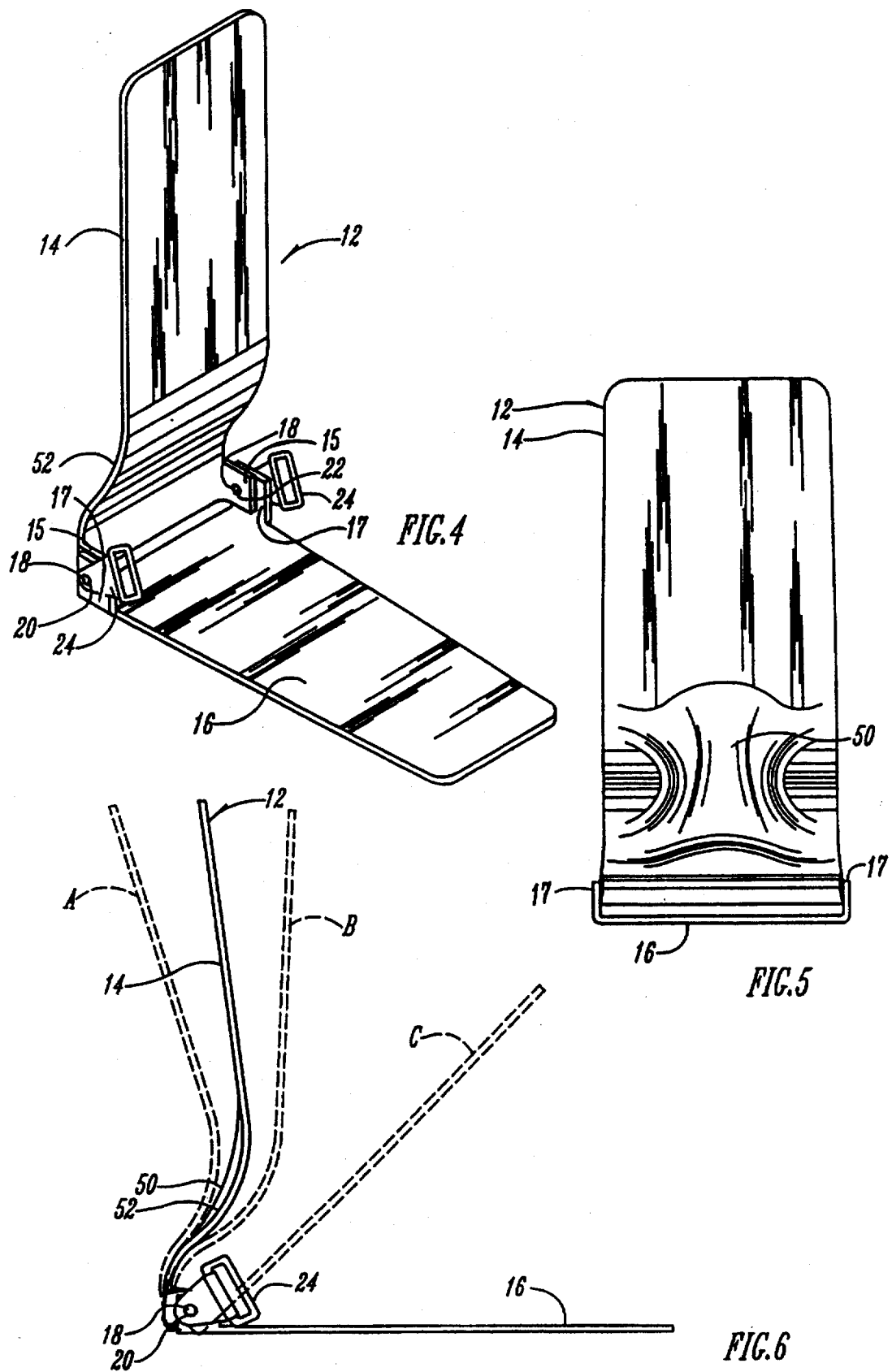

DEVICE FOR CORRECTING ANKLE CONTRACTURES

This is a continuation of application Ser. No. 08/209,242 filed on Mar. 14, 1994, now abandoned.

BACKGROUND OF THE INVENTION

The present invention relates to the field of therapeutic devices, in particular devices for correcting muscular problems such as plantar flexion contractures which can affect the human ankle joint.

Therapeutic devices for preventing drop foot (plantar flexion contracture of the ankle), maintaining the patient's foot in proper position, and for acting as a heel guard as well known in the art. For example, U.S. Pat. No. 3,345,654 illustrates a typical construction of such a device.

However, these devices are merely splints and are not primarily designed to correct an existing condition. They are not designed to apply a corrective pressure to the foot. As a matter of fact, their rigidity precludes their use to correct an existing condition.

Furthermore, they are not designed to act as a walking bracket or ambulation aid in gait training. This is important where the patient has been bed ridden for an extended period. This is especially true where the foot and leg have been held rigid.

Reissued U.S. Pat. No. Re. 33,762 discloses a therapeutic leg and foot device for correcting foot drop. The device can be utilized whether the patient is ambulatory or not. A steady corrective pressure is applied to the ankle area by virtue of the flexing of the integral L-shaped member. This pressure is automatically and instantaneously applied when the device is released against the inserted foot. Unfortunately for the patient, steady pressure can sometimes mean steady pain. Each patient has a different tolerance for such pain. Mobility of the joint also varies for each patient and over the course of treatment. The degree of mobility improvement is limited by the integral L-shape of the device. The one-steady-pressure-fits-all approach disclosed by U.S. Pat. No. Re. 33,762 does not provide the adjustability necessary to best serve and treat some patients.

Therefore, it is the primary object of this invention to provide a more comfortable device for correcting ankle contractures resulting in drop foot.

A further object of this invention is to provide a conveniently, quickly, and comfortably applicable device.

A further object of this invention is to provide a device wherein a washable, absorbent liner is removably interposed between the foot and leg on a pivotally connected two-piece L-shaped frame.

A further object of this invention is to provide a device for applying an adjustable amount of tension at obtuse, right, and acute angles of the ankle.

These and other objects should be apparent to one skilled in the art.

SUMMARY OF THE INVENTION

A therapeutic device for correcting ankle contractures affecting the angle between the leg and foot includes a generally L-shaped member having a leg portion and a foot portion pivotally connected to the leg portion. The device has a laterally split anklet having overlapping right and left flaps releasably fastenable to each other and pockets which slide over the free ends of the L-shaped member so as to be detachably connected thereto. The anklet wraps around parts of the foot and leg proximate to the ankle in order to cushion them against direct contact with the L-shaped member. A pair of tension adjusting straps are attached on opposite sides of the anklet so as to operatively extend between the leg portion and the foot portion for putting steady yet releasable pressure on them to limit the angle therebetween, such that the foot is drawn closer to the leg. An adjustable length ankle strap is mounted on the L-shaped member for securing the member to the patient's leg and foot. The anklet holds the leg and foot in position in the L-shaped member. Loops and hooks fasteners are utilized on the flaps and straps to provide the adjustability needed to accomplish their stated functions.

BRIEF DESCRIPTION OF THE DRAWINGS

FIG. 1 is a perspective view of the present invention as applied to the human foot and leg.

FIG. 2 is a side elevation view of the device of this invention with the patient's foot removed.

FIG. 3 is a top view of the device of this invention.

FIG. 4 is a perspective view of the pivotable frame of this invention.

FIG. 5 is a rear elevation view showing how the shape of the leg portion of the present invention is contoured to receive and conform to the calf and rear of the ankle.

FIG. 6 is a side elevation view showing the pivoting frame of the present invention.

DETAILED DESCRIPTION OF THE PREFERRED EMBODIMENT

The device of the present invention is an orthosis 10 for use on a human leg and foot, as shown in FIG. 1. Orthosis 10 has a L-shape pivotable frame or member 12, which includes an upright leg portion 14 and a horizontal foot portion 16. The leg portion 14 has an upper end and lower end, and opposite sides. The leg portion 14 also has a pair of forwardly extending ears or tabs 15 on the opposite sides adjacent the lower end. The foot portion 16 has a forward end and rearward end, and opposite sides. The foot portion 16 has a pair of upwardly extending tabs 17 on the opposite sides adjacent the rearward end. The tabs 15, 17 on each side are in an overlapping relationship, as best seen in FIG. 4. The tabs 15, 17 of leg portion 14 and foot portion 16 are connected by a pin or rivet 18 to define pivot axes 20 and 22, respectively. Rivet 18 also attaches a buckle means, preferably a pivotable rectangular-shape loop 24 to each side of L-shaped member 12. Preferably, portions 14 and 16 of member 12 are made of a lightweight, heat moldable, thermoplastic.

In FIG. 1, a washable foam liner or anklet 26 permeable to air and water is shown to be detachably mounted to the L-shaped member 12. Preferably anklet 26 is also soft and absorbent. The front of anklet 26 is split laterally and, as viewed by the patient, comprises overlapping upper right and left flaps 27, 29 which are adapted to wrap around the lower portion of the patient's leg. The laterally overlapping upper right and left flaps 27, 29 of anklet 26 are joined at the front of the patient's leg with a conventional loops and hooks fastener. Thus, orthosis 10 is quickly adjustable to the size of the patient's leg. A similar loops and hooks fastening means 28 adjustably and releasably joins laterally overlapping lower right and left flaps 31, 33 of anklet 26 to comfortably conform to the patient's foot. In addition to showing the fastened flaps 27, 29, 31, 33, FIG. 3 shows that anklet 26 covers the bottom interior of orthosis 10 so as to comfortably cushion the patient's foot and extends upwardly at the rear interior of orthosis 10 to cushion the leg.

Referring again to FIG. 1, a toe opening 30 is preferably provided in the lower portion of anklet 26 so that the patient's toes can protrude therefrom and air can circulate around them. However, it should be noted that the foot portion 16 of the orthosis extends beyond the patient's toes. Thus, the toes are protected from frontal impacts while the patient is ambulating and tight bed linens are kept off the toes if the patient is bedridden.

As best seen in FIG. 2, anklet 26 has upper and lower pockets 32 and 34 which slidably receive the upper and forward ends of leg portion 14 and foot portion 16, respectively. The ends of the L-shaped member can be inserted or removed from the pockets 32, 34 by pivoting the leg and foot portions towards one another, as shown in FIG. 6. Preferably pockets 32 and 34 are sewn on the back and bottom of anklet 26. However, straps or bands or other suitable means of detachably connecting anklet 26 to L-shaped member 12 could be used without detracting from the invention.

The anklet 26 is preferably made of a lightweight and absorbent material which can draw perspiration away from the patient's skin. Because the anklet and L-shaped member are separable, greater flexibility exists in choosing appropriate material for them. A washable anklet makes sterilization easier and reduces the risk of infections or rashes. The fabric liner breathes, absorbs perspiration, and allows air to circulate around the leg and foot.

A triangular-shaped loop 36 is shown in FIGS. 2 and 3 to be attached to each side of the upper portion of anklet 26 by suitable means, such as running a cloth loop 38 around one leg of the triangular-shaped loop then sewing both ends of loop 38 to anklet 26. A tension adjusting strap 40 is attached on each side of the anklet 26 adjacent the forward end thereof by sewing or other suitable conventional fastening means. Strap 40 extends upwardly and passes through triangular-shaped loop 36 before being doubled back on itself and releasably fastened with loops and hooks fastener 42.

A loop and lock ankle strap 44 is threaded through a pair of spaced-apart vertical slits 47 at each end of an elongated pad 46, thereby slidably attaching pad 46 to strap 44 as shown in FIGS. 1–3. Ankle strap 44 is elongated, having opposite ends which are further passed through the pivotable rectangular-shaped loops 24 then doubled back on themselves in order to engage loops and hooks fasteners 48 which are incorporated into the straps. It should be apparent from FIGS. 1 and 2 that anklet 26 and ankle strap 44 allow the patient's leg and foot to be comfortably and yet securely held in position in the leg and foot portions 14 and 16 of orthosis 10. Ankle strap 44 is also readily detachable in order to remove the patient's leg from orthosis 10 for bathing, examination, therapy, or other treatment.

The leg portion 14 is contoured and channeled, as shown in FIGS. 1–6, so as to comfortably receive the posterior region of the lower leg. As shown in FIGS. 2 and 4–6, leg portion 14 includes an arched depression just above the ankle bone and below the greater calf to act as a support and receive most of the weight concentration when the leg is prone. This area also supplies the counter force for the flexing pressure of the foot rest portion 16 as hereinafter described. It should be understood that the lower part of leg portion 14 is shaped so the leg takes any pressure during flexing of the ankle joint with orthosis 10. Therefore, no pressure is applied to the rear of the patient's heel as a result of applying tension with orthosis 10. Such pressure to the heel would tend to cause the foot to rotate sideways or take an unwanted turn from its normal position. Foot rest portion 16 is essentially flat and provides a suitable surface on which the patient can walk. FIG. 5 shows that the lower part of leg portion 14 is also contoured to receive and conform to the shape of the human ankle, particularly the heel and Achilles' tendon. Contoured protrusion 50 receives the rear of the ankle and thereby, with the aid of straps 40, 44 and anklet 26, helps stabilize the foot laterally.

In FIG. 6, member 12 is shown to be pivotable about pivot axes 20 and 22 from an initial contractured position "A" wherein there is an obtuse angle between leg portion 14 and foot portion 16 and a full range of motion position "B" wherein there is an acute angle between leg portion 14 and foot portion 16. In fact, leg portion 14 preferably pivots to a position "C", within less than 45° from foot portion 16, so the distal ends of portions 14 and 16 can be inserted into anklet pockets 32 and 34, respectively, to attach anklet 26 to frame 12.

OPERATION OF THE INVENTION

In order to use orthosis 10, portions 14 and 16 of the L-shaped member 12 are pivoted toward each other as shown in FIG. 6. The anklet 26 is placed in between portions 14 and 16, which are then inserted in pockets 32 and 34. The resulting assembly is best seen in FIG. 2, Flaps 27, 29, 31, 33 of anklet 26 are opened and ankle strap 44 and tension adjusting straps 40 are unfastened. The angle between portions 14 and 16 of member 12 is then adjusted to approximately conform to that of the patient's contracture-affected ankle. Typically, although not necessarily, this angle is obtuse, as designated by position "A" in FIG. 6. Orthosis 10 is then wrapped around the patient's leg, ankle and foot. Flaps 27, 29, 31, 33 are comfortably secured with loops and hooks fasteners 28. Next, the loop and lock ankle strap 44 (having already been threaded through slits 47 in pad 46 and secured at one end around rectangular-shaped loop 24) is fastened to the second loop 24 in order to comfortably secure the patient's ankle. Finally, tension adjusting straps 40 are threaded through triangular-shaped loops 36 on the same side of the orthosis to which the strap is attached and secured in position for the desired angle of the leg and foot portions.

Steady, but releasable and adjustable tension can be applied to the ankle joint at various angles thereof. Adjustability is achieved by adjusting the length of straps 40 and securing them in place with the loops and hooks fasteners 48 provided thereon. The effective length is measured from the end of strap 40 which is fixed on foot portion 16 to triangular shaped loop 36. The orthosis 10 should be gradually adjusted to maintain constant, mild pressure to the plantar surface of the foot until full range of movement is attained, or until no further progress is possible. It should be appreciated that the device is not limited to a particular pressure or maximum improvement angle by the material or structure chosen for its construction. No separate structures are required to increase or augment the pressure.

It should be understood that orthosis 10 can be used while the patient is walking, bedridden, or otherwise nonambulatory. For bathing, dressing, therapy, or other treatment the orthosis is quickly and easily removable. First, the free ends of straps 40 are unfastened to release the tension on the joint. Ankle strap 44 is unfastened and flaps 27, 29, 31, 33 are opened. The patient's leg and foot is then freely removable.

The free ends of straps 40 and loops 36 can also be situated to fasten at foot portion 16 rather than leg portion 14. For that matter, neither end of straps 40 would have to be fixedly attached, but could both have fasteners.

Therefore, it can be seen that the present invention at least accomplishes its stated objectives.

What is claimed is:

1. A therapeutic leg and foot device, comprising:

a two-piece substantially L-shaped member including a leg portion and a foot portion;

the leg portion having upper and lower ends and opposite sides with a pair of tabs extending forwardly from the respective sides;

the foot portion having forward and rearward ends and opposite sides with a pair of tabs extending upwardly from the respective sides;

the tabs on each side of the foot and leg portions being in overlapping orientation to one another;

a pin extending through the overlapped tabs on each side of the foot and leg portions so as to define a pivot axis about which the foot and leg portions are pivotal and an adjustable angle between the foot and leg portions;

an anklet attached to the foot and leg portions and being adapted to receive a patient's foot and lower leg and retain the foot and lower leg in position relative to the foot and leg portions; and tension members operatively extending between the foot and leg portions to limit the angle therebetween.

2. The device of claim 1 wherein the anklet extends substantially over the foot and leg portions of the L-shaped member.

3. The device of claim 1 wherein the anklet has a foot pocket for receiving the forward end of the foot portion and a leg pocket for receiving the upper end of the leg portion.

4. The device of claim 1 wherein the tension members are adjustably attached to the anklet on opposite sides thereof.

5. The device of claim 1 further comprising an ankle strap adjustably connected to the L-shaped member and being adapted to retentively extend over the patient's ankle.

6. The device of claim 1 wherein the pivot axis is behind the patient's heel.

7. The device of claim 1 wherein the leg portion is contoured to the shape of the patient's ankle.

8. A therapeutic leg and foot device, comprising:

a substantially L-shaped member including a leg portion and a foot portion, the leg and foot portions being separate components pivotally connected together to form the L-shaded member;

the leg portion having upper and lower ends and opposite sides;

the foot portion having forward and rearward ends with opposite sides;

an anklet attached to the foot and leg portions and being adapted to receive a patient's foot and lower leg and retain the foot and lower leg in position relative to the foot and leg portions; and the leg portion having a contoured portion corresponding to the patient's Achilles' tendon.

9. The device of claim 8 wherein the lower end of the leg portion and the rearward end of the foot portion being joined to define a transverse pivot axis about which the foot and leg portions are pivotal and an adjustable angle between the foot and leg portions.

10. The device of claim 8 further comprising tension members adjustably attached to opposite sides of the anklet to control the angle between the foot and leg portions of the L-shaped member.

11. The device of claim 8 wherein the anklet has a foot pocket for receiving the forward end of the foot portion and a leg pocket for receiving the upper end of the leg portion.

12. The device of claim 8 further comprising an ankle strap adjustably connected to the L-shaped member and being adapted to retentively extend over the patient's ankle.

13. The device of claim 8 wherein the pivot axis is behind the patient's heel.

14. A therapeutic leg and foot device, comprising:

a substantially L-shaped member including a leg portion and a foot portion;

the leg portion having upper and lower ends and opposite sides;

the foot portion having forward and rearward ends with opposite sides;

the lower end of the leg portion and the rearward end of the foot portion being joined to define a transverse pivot axis about which the foot and leg portions are pivotal and an adjustable angle between the foot and leg portions;

an anklet attached to the foot and leg portions and being adapted to receive a patient's foot and lower leg and retain the foot and lower leg in position relative to the foot and leg portions;

flexible tension members adjustably attached to opposite sides of the anklet to control the angle between the foot and leg portions of the L-shaped member; and the anklet extending substantially over the foot and leg portions of the L-shaped member.

15. The device of claim 14 wherein the anklet has a foot pocket for receiving the forward end of the foot portion and a leg pocket for receiving the upper end of the leg portion.

16. The device of claim 14 further comprising an ankle strap adjustably connected to the L-shaped member and being adapted to retentively extend over the patient's ankle.

17. The device of claim 14 wherein the pivot axis is behind the patient's heel.

18. The device of claim 14 wherein the leg portion has a contoured portion corresponding to a patient's Achilles' tendon.

19. The device of claim 14 wherein the foot and leg portions comprise two pieces, and further comprising a pair of tabs extending forwardly from the opposite sides of the leg portion adjacent the lower end thereof, a pair of tabs extending upwardly from the opposite sides of the foot portion adjacent the rearward end thereof, the tabs on each side of the foot and leg portions being in an overlapping orientation to one another, and pins extending through the overlapped tabs on each side of the foot and leg portions, the pins defining the pivot axis.

20. A therapeutic leg and foot device, comprising:

a substantially L-shaped member including a leg portion and a foot portion;

the leg portion having upper and lower ends and opposite sides;

the foot portion having forward and rearward ends with opposite sides;

the lower end of the leg portion and the rearward end of the foot portion being joined to define a transverse pivot axis about which the foot and leg portions are pivotal and an adjustable angle between the foot and leg portions;

an anklet attached to the foot and leg portions and being adapted to receive a patient's foot and lower leg and retain the foot and lower leg in position relative to the foot and leg portions;

flexible tension members adjustably attached to opposite sides of the anklet to control the angle between the foot and leg portions of the L-shaped member; and the anklet having a foot pocket for receiving the forward end of the foot portion and a leg pocket for receiving the upper end of the leg portion.

21. The device of claim 20 wherein the anklet extends substantially over the foot and leg portions of the L-shaped member.

22. The device of claim 20 further comprising an ankle strap adjustable connected to the L-shaped member and being adapted to rententively extend over the patient's ankle.

23. The device of claim 20 wherein the pivot axis is behind the patient's heel.

24. The device of claim 20 wherein the leg portion has a contoured portion corresponding to a patient's ankle.

25. The device of claim 20 wherein the foot and leg portions comprise two pieces, and further comprising a pair of tabs extending forwardly from the opposite sides of the leg portion adjacent the lower end thereof, a pair of tabs extending upwardly from the opposite sides of the foot portion adjacent the rearward end thereof, the tabs on each side of the foot and leg portions being in an overlapping orientation to one another, and pins extending through the overlapped tabs on each side of the foot and leg portions, the pins defining the pivot axis.

26. A therapeutic leg and foot device, comprising:
   a substantially L-shaped member including a leg portion and a foot portion;
   the leg portion having upper and lower ends and opposite sides;
   the foot portion having forward and rearward ends with opposite sides;
   the lower end of the leg portion and the rearward end of the foot portion being joined to define a transverse pivot axis about which the foot and leg portions are pivotal and an adjustable angle between the foot and leg portions;
   an anklet attached to the foot and leg portions and being adapted to receive a patient's foot and lower leg and retain the foot and lower leg in position relative to the foot and leg portions;
   flexible tension members adjustably attached to opposite sides of the anklet to control the angle between the foot and leg portions of the L-shaped member; and
   the leg portion having a contoured portion conforming to the shape of a patient's Achilles tendon.

27. The device of claim 26 further comprising an ankle strap adjustable connected to the L-shaped member and being adapted to retentively extend over the patient's ankle.

28. The device of claim 26 wherein the pivot axis is behind the patient's heel.

29. The device of claim 26 wherein the foot and leg portions comprise two pieces, and further comprising a pair of tabs extending forwardly from the opposite sides of the leg portion adjacent the lower end thereof, a pair of tabs extending upwardly from the opposite sides of the foot portion adjacent the rearward end thereof, the tabs on each side of the foot and leg portions being in an overlapping orientation to one another, and pins extending through the overlapped tabs on each side of the foot and leg portions, the pins defining the pivot axis.

30. A therapeutic leg and foot device, comprising:
   a substantially L-shaped member including a leg portion and a foot portion;
   the leg portion having upper and lower ends and opposite sides;
   the foot portion having forward and rearward ends with opposite sides;
   the lower end of the leg portion and the rearward end of the foot portion being joined to define a transverse pivot axis about which the foot and leg portions are pivotal and an adjustable angle between the foot and leg portions;
   an anklet attached to the foot and leg portions and being adapted to receive a patient's foot and lower leg and retain the foot and lower leg in position relative to the foot and leg portions;
   flexible tension members adjustably attached to opposite sides of the anklet to control the angle between the foot and leg portions of the L-shaped member; and
   the foot and leg portions comprising two pieces, and further comprising a pair of tabs extending forwardly from the opposite sides of the leg portion adjacent the lower end thereof, a pair of tabs extending upwardly from the opposite sides of the foot portion adjacent the rearward end thereof, the tabs on each side of the foot and leg portions being in an overlapping orientation to one another, and pins extending through the overlapped tabs on each side of the foot and leg portions, the pins defining the pivot axis.

* * * * *